US006638723B1

(12) United States Patent
Kim

(10) Patent No.: US 6,638,723 B1
(45) Date of Patent: Oct. 28, 2003

(54) METHOD FOR DIAGNOSING AUTOIMMUNE DISEASES

(76) Inventor: Think You Kim, 7-1207, Hanyang Apartment, Jayang-dong, Kwangjin-ku, Seoul 143-190 (KR)

( * ) Notice: Subject to any disclaimer, the term of this patent is extended or adjusted under 35 U.S.C. 154(b) by 71 days.

(21) Appl. No.: 09/000,490

(22) PCT Filed: Aug. 6, 1996

(86) PCT No.: PCT/KR96/00132

§ 371 (c)(1),
(2), (4) Date: Feb. 9, 1998

(87) PCT Pub. No.: WO97/06440

PCT Pub. Date: Feb. 20, 1997

(30) Foreign Application Priority Data

Aug. 7, 1995 (KR) ............................................. 95-24341

(51) Int. Cl.[7] ...................... G01N 33/53; G01N 33/554; G01N 33/564
(52) U.S. Cl. ...................... 435/7.1; 435/7.24; 435/7.95; 435/40.5; 435/40.51; 435/174; 435/325; 435/372; 435/960; 435/973; 436/506; 436/508; 436/509; 436/519; 436/63; 436/172; 436/811
(58) Field of Search ................................. 435/7.1, 7.21, 435/7.24, 7.95, 40.5, 40.51, 40.52, 174, 960, 6, 973, 325, 372; 436/506, 508, 509, 518, 519, 527, 63, 172, 811

(56) References Cited

U.S. PATENT DOCUMENTS 5,985,578 A * 11/1999 Pestronk ..................... 435/7.1

OTHER PUBLICATIONS

Archer et al., 1994 Deconstructing the microtubule organizing center. Cell 76: 589–591. (Reference #8 attached to applicant's response filed Jul. 26, 2000).*
McCarty et al., 1984. Antibody to the mitotic spindle apparatus: immunologic characteristics and cytologic studies. J. Rheumatol. 11: 213–218.*
McCarty, G.A., 1986. Autoantibodies and their relation to rheumatic diseases. Medical Clinics of North America 70: 237–261.*
Yin Pei Hong et al., 1994. Studies on the centrosome antiserum from a scleroderma patient. Acta Biologiae Experimentalis Sinica 25: 483–495. Translated from Chinese.*
Glover et al., 1993. The centrosome. Scientific American, issued Jun. 1993, pp. 32–38.*
Geiger et al., 1982. Spatial relationships of microtubule–organizing centers and the contact area of cytotoxic T lymphocytes and target cells. Journal of Cell Biology 95: 137–143, Oct. 1982.*
Rousset et al., 1983. Anti–tubulin antibodies in autoimmune thyroid disorders. Clin. Exp. Immunol. 52: 325–332.*
Rousset et al., 1984. Anti–tubulin antibodies in recent onset Type 1 (insulin–dependent) diabetes mellitus: comparison with islet cell antibodies. Diabetologia 27: 427–432.*
Franch et al., Mar. 1994. Anticytoskeletal autoantibody development in adjuvant arthritis. J. Rheumatol. 21: 489–97.*
McCarty et al., Nov. 1982. A unique autoantibody to the mitotic spindle apparatus. J. Cell Biol. 95: 353a, Abstract#17079.*
Tuffanelli et al., Jul. 1983. Anticentromere and anticentriole antibodies in the scleroderma spectrum. Arch. Dermatol. 119:560–566.*
Balczon et al., 1991. The identification of mammalian centrosomal antigens using human autoimmune anticentrosome antisera. Cell MOtility and Cytoskeltoen 20: 121–135.*
Nakamura et al., 1994. Current status of available standards for quality improvement of assays for detection of autoantibodies to nuclear and intracellular antigens. J. Clin. Lab Anal. 8: 360–368.*
ARA Glossary Committee, Dictionary of the Rheumatic Disease, vol. II: Diagnostic Testing, 1985, pp. 17.
Molecular Biology of The Cell, 3rd Edition, Garland, pp. 789–795. Alberts et al, eds.
Molecular Cell Biology, 3rd Edition, pp. 1067–1070. Lodish et al., eds. New York: Scientific American Books.

* cited by examiner

Primary Examiner—Christopher L. Chin
Assistant Examiner—James L. Grun

(57) ABSTRACT

A method of diagnosing an autoimmune disease is disclosed which involves determining whether autoantibodies from a body fluid react with a microtubule organizing center (MTOC). This diagnostic procedure provides a simple, highly specific, and highly reliable diagnosis of autoimmune disease, including rheumatoid arthritis.

5 Claims, 1 Drawing Sheet

METHOD FOR DIAGNOSING AUTOIMMUNE DISEASES

BACKGROUND OF THE INVENTION

1. Field of the Invention

The present invention is related to a novel diagnostic method of autoimmune diseases. More specifically, the present invention is related to a novel method of diagnosing autoimmune diseases by immunologically detecting antibodies to microtubule organizing center (hereinafter, referred to as "MTOC") and/or microtubules extending therefrom and/or accompanying proteins present in human and animal tissues or cells.

2. Description of the Prior Arts

An autoimmune disease, an immune system disorder causing formation of antibodies against endogenous materials and not against foreign materials, may be classified into two categories: systemic rheumatic diseases and organ-specific autoimmune diseases. The systemic rheumatic diseases again may be classified into many kinds of diseases including systemic lupus erythematosus, rheumatoid arthritis, or the like.

Rheumatoid arthritis is a very frequently occurring disease, which is found in 1–5% of the world's populations. Its typical symptoms include morning stiffness and joint pains of the hands and feet.

Since the etiology of rheumatoid arthritis is still unknown, its successful therapy or accurate diagnosis is not easy.

Until now, the rheumatoid factor has been detected to diagnose rheumatoid arthritis. However, the rheumatoid factor is not detected in all patients with the disease, and furthermore, shows positive results in about 5–20% of normal persons. (ARA Glossary Committee, Dictionary of the rheumatic disease 11, diagnostic testing, p. 17, 1985).

To avoid these problems, anti-keratin, anti-perinuclear factor and anti-RA-33 antibodies were developed. These antibodies contributed in improving the diagnostic specificity of rheumatoid arthritis. However, the sensitivity is still low to use in practice.

In particular, the ANA test ("Anti-nuclear antibody test") has been the most widely used test in diagnosing autoimmune diseases. However, the conventional ANA test employing the HEp-2 cell line is mainly directed to detect systemic lupus erythematosus. Therefore, it is necessary to detect the rheumatoid factor separately in order to diagnose rheumatoid arthritis.

The present inventor had found that a macrophage is more useful than the conventionally used HEp-2 cell to diagnose autoimmune diseases, and succeeded in establishing a macrophage cell line. The established cell line was named "IT-1" and was deposited on Jul. 15, 1992, at the Korean Culture Collection of Microorganisms, Yonsei University located in Seoul, Korea, under Accession No. KFCC 10772 according to the Budapest Treaty.

As a result of continuing extensive research, the present inventor surprisingly found that body fluids of patients with rheumatoid arthritis characteristically contain antibodies against microtubule organizing center ("MTOC") and/or microtubules ("MT") extending therefrom.

SUMMARY OF THE INVENTION

Thus, an object of the present invention is to provide a method for diagnosing autoimmune diseases with high specificity and sensitivity.

Another object of the present invention is to provide a method for diagnosing autoimmune diseases comprising steps of:

contacting a body fluid sample of a subject suspected to have an autoimmune disease with any living tissue or cell line; and determining whether or not MTOC and/or MT and/or accompanying proteins have reacted with anti-MTOC-MT antibodies in the body fluid.

The present invention also provides a method for detecting anti-nuclear antibody, anti-cytoplasmic antibody and anti-MTOC-MT antibodies simultaneously by using a tissue or cell.

The present invention further provides a method for diagnosing autoimmune diseases comprising the following steps:

preparing a glass slide, on which a tissue or cell is immobilized;

preparing a body fluid sample of a subject suspected to have an autoimmune disease;

contacting the body fluid sample with the tissue or cell on the glass slide and incubating at a certain temperature for a certain period of time; and detecting the presence of anti-MTOC-MT antibodies, which respond to the MTOC, MT or accompanying proteins in the tissue or cell.

BRIEF DESCRIPTION OF DRAWINGS

This invention will be described in more detail with reference with accompanying drawings in which.

Figure 1:
FIG. 1 is a fluorescent microscopic picture showing anti-MTOC-MT antibodies detected by an indirect immunofluorescence technique using the IT-1 cell. The MTOC is located near the nucleus of the IT-1 cell, and thread-like MT extending from the MTOC can be seen.

The above and other objects, features and applications of the present invention will be apparent to those skilled in the art from the following detailed explanation.

DETAILED EXPLANATION OF THE INVENTION

The present invention is based on the inventor's surprising findings that the body fluids of patients with rheumatoid arthritis characteristically contain autoantibodies against microtubule organizing center ("MTOC"), and/or microtubules ("MT") extending therefrom, and/or proteins accompanying MTOC and MT. The MTOC, MT and accompanying proteins occur in all of the tissues or cells originating from animals including human beings. Moreover, it is strongly expected that the MTOC, MT and accompanying proteins occur in insects.

The term "anti-MTOC-MT antibodies" employed throughout the application means and includes all antibodies to MTOC, MT, proteins accompanying MTOC and proteins accompanying MT. This is based on the fact that autoantibodies in the body fluid of patients with autoimmune diseases can immunologically respond to one, two or all of the MTOC, MT and accompanying proteins. Herein, the antibodies are autoantibodies and present in patients with autoimmune diseases, particularly body fluids of patients with rheumatoid arthritis.

For the present invention, the origin and kind of tissues or cells that serve as a source of MTOC, MT and accompanying proteins which react with anti-MTOC-MT antibodies of patients with a autoimmune diseases is not particularly limited. The MTOC, MT and accompanying proteins occur in all tissues or cells of humans, animals such as rats, mice, rabbits, cows, and insects. As for the kind of the tissues or cells, for the purpose of simple and easy use, any established tissue or cell may be advantageously used. For example, the IT-1 cell line (KFCC 10772), an established macrophage cell line provided by the present inventor may advantageously be used. Or a human cancer cell such as HEp-2 (deposited at ATCC under accession number CCL 23 or commercially available) can be advantageously employed. In particular, the IT-1 cell line can be more advantageously used, since it renders a more accurate and clearer detection of the MTOC and MT of patients with autoimmune diseases.

Moreover, for more convenient applications, the tissues or cells can be immobilized onto a glass slide. Immobilization of human tissues or cells on the glass slide can be carried out by using conventional methods. The parameters such as time, temperature and fixatives may be chosen without difficulty by those skilled in the technique and do not limit the present invention. As fixatives, organic solvents such as ethanol, acetone, or methanol, and cross-linking reagents such as paraformaldehyde or glutaraldehyde, in single or as mixtures thereof may advantageously be employed.

When the tissues or cells are immobilized on the glass slide, the tissues or cells may be treated to remove their cell wall in order to attain an easy and clear reading of the results. For this purpose, surface active agents such as Triton-X™ may be employed.

The results of immunological reactions between MTOC, MT and/or accompanying proteins in tissues or cells and anti-MTOC-MT antibodies in patients can be detected by using any conventional technique employed for detecting immunological reactions. Indirect immunofluorescence technique, immunoenzyme technique and radioimmunoassay, for example, can be used.

Until now, as described above, two or more separate tests, e.g., ANA (Anti-Nuclear Antibody) test plus rheumatoid factor had to be carried out to obtain a reliable result for autoimmune disease diagnosis. In contrast, the present invention allows use of established cell lines such as human macrophage IT-1 or human cancer cell HEp-2 to be used as human tissues or cells to detect not only anti-MTOC-MT antibodies but also anti-nuclear antibodies simultaneously, thereby making it possible to detect a more broad spectrum of autoimmune diseases including rheumatoid arthritis.

The body fluid of patients with autoimmune diseases may include, but not limited thereto, blood samples such as whole blood, serum, or plasma, synovial fluids, cerebrospinal fluids, or pleural fluids.

The method for diagnosing rheumatoid arthritis using tissues or cell lines will be described in more detail hereinafter.

A glass slide having a tissue or cell line immobilized thereon is prepared. A series of two-fold dilutions (each 30 microliters) (from 1:20 to 1:1280 dilutions) of body fluid from a patient with rheumatoid arthritis are dropped onto the glass slide. After allowing to react at room temperature and high humidity for about 30 minutes, the glass slide is placed into a Coplin jar containing phosphate buffered saline (PBS), agitated at 200 rpm using an agitator, washed and dried. Thirty microliters of a dilution (1:40) of fluorescein-conjugated polyvalent anti-human immunoglobulin (Dako) is dropped on the slide, which is then allowed to react at room temperature and high humidity for about 30 minutes. After washing the slide with PBS, the slide is counter-stained by using 0.2% Evans' blue (Sigma) and washed with PBS.

The excessive buffer is removed using an absorptive paper, a PBS-glycerol solution is mounted thereon, and observed under a fluorescent microscope.

Circular or ring-shaped fluorescent patterns of the MTOC are observed near the nucleus. The thread-like MTs extending from the MTOC are also observed (FIG. 1). Such patterns are morphological characteristics of the MTOC and MT, respectively (Molecular Biology of the Cell, 3rd Ed., Garland, pp 789–795).

Antibodies detected in the body fluid of patients with autoimmune disease, particularly, rheumatoid arthritis are presumed to be antibodies against MTOC, MT and accompanying proteins. The present inventor named the fluorescent pattern in FIG. 1 as "perinuclear single large granular with skeleton", which is a characteristic of rheumatoid arthritis.

PREFERRED EMBODIMENTS OF THE INVENTION

The present invention will be embodied by way of the following examples. However, these examples are provided for the illustration purpose only and should not be construed as limiting the scope of the invention, which is properly delineated in the accompanying claims. The parts or percents in the Examples are based on the weight, unless indicated otherwise.

Example 1

$2 \times 10^4$ cells/ml of IT-1 cell line (KFCC 10772) cultured in RPMI-1640 supplemented with 10% bovine serum were placed into wells of glass slides. The cells were grown in an incubator under 5% $CO_2$ atmosphere at 37° C. for 24 hours. The culture media was removed from the slides, and the slides were washed with PBS and immersed into an acetone-methanol mixture (1:1) for 5 minutes for fixation.

Serum samples from 269 patients with rheumatoid arthritis, which were stored at −70° C., were successively diluted two-fold from 1:20 to 1:1280.

Thirty microliters of each dilution was dropped on the slides and allowed to react at room temperature and high humidity for 30 minutes.

The glass slides were then placed into a Coplin jar containing PBS, and agitated at 200 rpm using an agitator, washed and dried. Thirty microliters of a dilution (1:40) of fluorescein-conjugated polyvalent anti-human immunoglobulin (Dako) was dropped on the slides, which were then allowed to react at room temperature and high humidity for about 30 minutes. After washing the slides with PBS, the slides were counter-stained by using 0.2% Evans' blue (Sigma) and washed with PBS. The excessive PBS was removed using an absorptive paper, a PBS-glycerol solution was mounted thereon, and observed under a fluorescent microscope.

The result is shown in FIG. 1. Circular or ring-shaped fluorescent patterns of the MTOC were observed near the nucleus. The thread-like MT extending from the MTOC, were also observed. That is to say, the pattern of "perinuclear single large granular with skeleton" was observed.

Comparative Example 1
Diagnosis of Rheumatoid Arthritis through Rheumatoid Factor Test 0.05 ml of serum samples, which were the same as those used in Example 1, were dropped onto a glass slide, and the same amount of human gamma globulin emulsion (Iatron)

was added thereto. The mixture was mixed well and allowed to stand for 1 minute. Then, the glass slide was gently shaken in a horizontal direction and any aggregation was observed.

Results 148 (55%) among 269 samples showed positive reactions in the inventive test (Example 1) and rheumatoid factor test (Comparative Example 1). 62 (23%) samples were negative in rheumatoid factor test and positive in the inventive test, while 42 (16%) samples were positive in rheumatoid factor test and negative in the inventive test. And, 17 samples (6%) were negative in both tests.

These results indicate that the inventive method is highly sensitive compared with the conventional rheumatoid factor test, thereby significantly reducing the probability of false negative results.

Example 2

The procedures in Example 1 and Comparative Example 1 were carried out using blood samples of 125 normal human beings.

At 1:20 dilution, the inventive test gave 4% (5 among 125) positive results, while the rheumatoid factor test gave 9.6% (12 among 125) positive results. Accordingly, it can be proven that the inventive method using anti-MTOC-MT antibodies reduces the probability of false positive results. Therefore, the inventive method can increase specificity.

Example 3

Blood samples of twelve patients showing positive results in both of the inventive and rheumatoid factor tests were prepared. The procedure of Example 1 was carried out using the same blood samples on commercially available HEp-2 cells purchased from Kallestad (USA) or MBL (Japan) instead of the IT-1 cells.

Both experiments gave positive anti-MTOC-MT antibody results. However, HEp-2 cells from the two companies showed weaker fluorescence than the IT-1 cell line of Example 1. Moreover, tests using HEp-2 cells showed only very small-sized-MIOCs

Example 4

The procedure of Example 1 was carried out with the exception that the IT-1 cell line was fixed with a mixture of 4% paraformaldehyde/0.2% Triton-X, or treated with 0.5% Triton-X, respectively. The results showed more clear fluorescent patterns when treated with 0.5% Triton-X.

Example 5

Patients with rheumatoid arthritis usually experience articular edema and an increase of synovial fluid. So, synovial fluid may be used to detect anti-MTOC-MT antibodies.

The procedure of Example 1 was carried out with the exception that synovial fluid from ten patients with rheumatoid arthritis was used. As a result, all synovial samples showed positive results.

Example 6

The procedure of Example 1 was carried out with the exception that McCoy cells (ATCC CRL 1696) and a macrophage cell line of mouse origin (RAW cell, ATCC TIB 71) were used instead of the ITI-1 cells.

These cells were used to make the glass slides on which sera from twelve patients known to be anti-MTOC-MT positive were applied. These mouse cell lines showed the MTOCs to be much smaller compared to those seen with the IT-1 cells, but the MT showed positive results.

What is claimed is:

1. A method for diagnosing an autoimmune disease, comprising:
   (a) contacting a body fluid of a subject suspected of having an autoimmune disease with a cell having a cytoplasmic microtubule organizing center (MTOC); and
   (b) determining whether said MTOC has reacted with autoantibodies (anti-MTOC antibodies) in the body fluid, wherein said reaction is diagnostic of autoimmune disease in the subject, and
   wherein said cell is a macrophage selected from an IT-1 cell line deposited as KFCC 10772.

2. The method of claim 1, wherein said autoimmune disease is rheumatoid arthritis.

3. The method of claim 1, wherein the determining step is carried out by indirect immunofluorescence.

4. The method of claim 3, wherein said indirect immunofluorescence gives a fluorescent pattern of perinuclear single large granular with skeleton.

5. The method of claim 1, which further comprises detecting anti-microtubule antibodies, anti-nuclear antibodies or anti-cytoplasmic antibodies other than anti-MTOC antibodies.

* * * * *